United States Patent
Xu et al.

(10) Patent No.: US 11,944,395 B2
(45) Date of Patent: Apr. 2, 2024

(54) 3D VISUALIZATION ENHANCEMENT FOR DEPTH PERCEPTION AND COLLISION AVOIDANCE

(71) Applicant: Verb Surgical Inc., Santa Clara, CA (US)

(72) Inventors: Yiming Xu, Sunnyvale, CA (US); Berk Gonenc, San Jose, CA (US)

(73) Assignee: Verb Surgical Inc., Santa Clara, CA (US)

( * ) Notice: Subject to any disclaimer, the term of this patent is extended or adjusted under 35 U.S.C. 154(b) by 834 days.

(21) Appl. No.: 17/014,092

(22) Filed: Sep. 8, 2020

(65) Prior Publication Data

US 2022/0071716 A1    Mar. 10, 2022

(51) Int. Cl.
| | |
|---|---|
| *A61B 34/10* | (2016.01) |
| *A61B 1/00* | (2006.01) |
| *A61B 34/00* | (2016.01) |
| *A61B 34/35* | (2016.01) |
| *G06N 20/00* | (2019.01) |
| *A61B 34/30* | (2016.01) |

(52) U.S. Cl.
CPC .......... *A61B 34/25* (2016.02); *A61B 1/0005* (2013.01); *A61B 1/00055* (2013.01); *A61B 1/00193* (2013.01); *A61B 34/35* (2016.02); *G06N 20/00* (2019.01); *A61B 2034/301* (2016.02)

(58) Field of Classification Search
CPC ....... A61B 34/25; A61B 34/35; A61B 1/0005; A61B 1/00055; A61B 1/00193; A61B 2034/301; G06N 20/00

USPC .......................................................... 382/128
See application file for complete search history.

(56) References Cited

U.S. PATENT DOCUMENTS

| | | | |
|---|---|---|---|
| 11,191,423 B1* | 12/2021 | Zingaretti | A61B 1/01 |
| 2011/0301447 A1* | 12/2011 | Park | G06T 7/0016 600/407 |
| 2012/0294498 A1 | 11/2012 | Popovic | |
| 2013/0345509 A1 | 12/2013 | Alamaro et al. | |
| 2014/0163359 A1* | 6/2014 | Sholev | A61B 1/00011 600/407 |
| 2014/0336461 A1 | 11/2014 | Reiter et al. | |
| 2017/0181798 A1 | 6/2017 | Panescu et al. | |
| 2018/0296281 A1 | 10/2018 | Yeung et al. | |

FOREIGN PATENT DOCUMENTS

| | | |
|---|---|---|
| JP | 2016518156 | 6/2016 |
| WO | 2017209905 | 12/2017 |

OTHER PUBLICATIONS

International Search Report and Written Opinion for International Application No. PCT/US2020/050915 dated May 10, 2021, 17 pages.

\* cited by examiner

*Primary Examiner* — Gabriel I Garcia
(74) *Attorney, Agent, or Firm* — Aikin & Gallant, LLP

(57) ABSTRACT

A series of images is obtained from an endoscope. Three-dimensional reconstruction is performed on the series of images to reconstruct anatomy shown in the series of images. A graphic, such as a grid, is rendered based on the three-dimensional reconstruction, over the series of images resulting in an enhanced endoscopic video feed to be shown on a display.

19 Claims, 6 Drawing Sheets

3D VISUALIZATION ENHANCEMENT FOR DEPTH PERCEPTION AND COLLISION AVOIDANCE

TECHNICAL FIELD

This disclosure relates generally to the field of surgical robotics and, more particularly, to generating a visual enhancement for depth perception or collision avoidance.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more tools and at least one endoscopic camera through the incisions into the patient. The surgical procedures are then performed by using the introduced tools, with the visualization aid provided by the camera.

Generally, MIS provides multiple benefits, such as reduced patient scarring, less patient pain, shorter patient recovery periods, and lower medical treatment costs associated with patient recovery. In some embodiments, MIS may be performed with surgical robotic systems that include one or more robotic arms for manipulating surgical tools based on commands from an operator. For example, an operator may provide commands for manipulating surgical tools, while viewing an image that is provided by a camera and displayed on a display to the user.

As described above, MIS can include inserting an endoscope into a patient to provide imagery of the internal anatomy of a patient during surgery. A minimally invasive surgical tool is inserted into the patient within the view of the endoscope. The endoscope view allows a surgeon to see the tool so that the tool can be moved and manipulated, such as, for example, to perform cutting, grabbing, or suturing.

During teleoperation, current 3D endoscopic view can provide perception of depth and distance with the binocular cues. This allows the user to judge the relative positions between the workspace and the tools. However, such a system can become ineffective. Depending on the endoscopic viewpoints, lighting conditions, and textures in the workspace, the user may struggle to gauge the distances of objects and tools. This poses a challenge to new users and experienced users alike. This problem can be exacerbated when using a standard two-dimensional display, due to a lack of spatial cues. Uncertainty of distances shown in an endoscopic view, regardless of whether shown on a three dimensional stereoscopic display or on a standard two-dimensional display, could lead to slower performance of the surgery due to uncertainty—a user might perform the surgery slower to maintain accuracy or reduce the risk of unwanted contact between tools or between a tool and patient anatomy.

SUMMARY

Endoscopic visualization during teleoperation or for manually performed operations can be enhanced. A system and method can render graphics over an existing endoscopic view, which can include a pattern (e.g., 3D gridlines or a mesh) that shows or enhances the visibility of the shape and contours of surfaces detected in the endoscopic image feed. Graphics can include geometric references of the surgical tool positions. Such references can help a viewer discern position of the tool relative to the tissue, organ, and other internal anatomy of the patient. Such a system can reinforce the user's depth perception of the endoscopic scene and the relative distances between the tools and the environment. The endoscopic scene is the environment that is captured by image sensors of the endoscope. For example, when inserted in a patient, the endoscopic scene can include a patient's anatomy such as tissue, organs, muscle, bone, etc.

In some embodiments a method is performed that improves depth perception of an endoscopic view. The method includes obtaining a series of images obtained from an endoscope, in other words, an endoscopic video feed. Three-dimensional reconstruction is performed on the series of images to reconstruct anatomy shown in the series of images. A graphic (e.g., a pattern, a grid, etc.) is rendered based on the three-dimensional reconstruction, over the series of images resulting in an enhanced endoscopic video feed to be shown on a display. This method can be performed with a surgical robotic system, and/or manual minimally invasive surgical tools. In such a manner, the user's operation performance can be improved and unintentional collisions, such as between tools or between tools and internal anatomy, can be reduced.

The graphical visualization enhancement can be displayed on a three dimensional display (e.g., a stereoscopic display) rendered over or 'on top of' the endoscopic views. The 3D reconstructed scene can also be utilized in a virtual reality or augmented reality setup (e.g., with a head worn display) for teleoperation, simulation, or training scenarios. Additionally, or alternatively, the enhancement (e.g., geometric gridlines and positional references) may also be implemented on a standard two-dimensional screen and provide monocular cues of the three-dimensional scene. The graphical overlay could be enabled or disabled by the user, either fully or partially, through user input devices such as a handheld controller, a graphical user interface, speech recognition, or other equivalent input means.

The above summary does not include an exhaustive list of all embodiments of the present disclosure. It is contemplated that the disclosure includes systems and methods that can be practiced from all suitable combinations of the various embodiments summarized above, as well as those described in the Detailed Description below and particularly pointed out in the Claims section. Some combinations may have particular advantages not specifically recited.

DETAILED DESCRIPTION

Non-limiting examples of various embodiments and variations of the invention are described herein and illustrated in the accompanying drawings.

Figure 1:
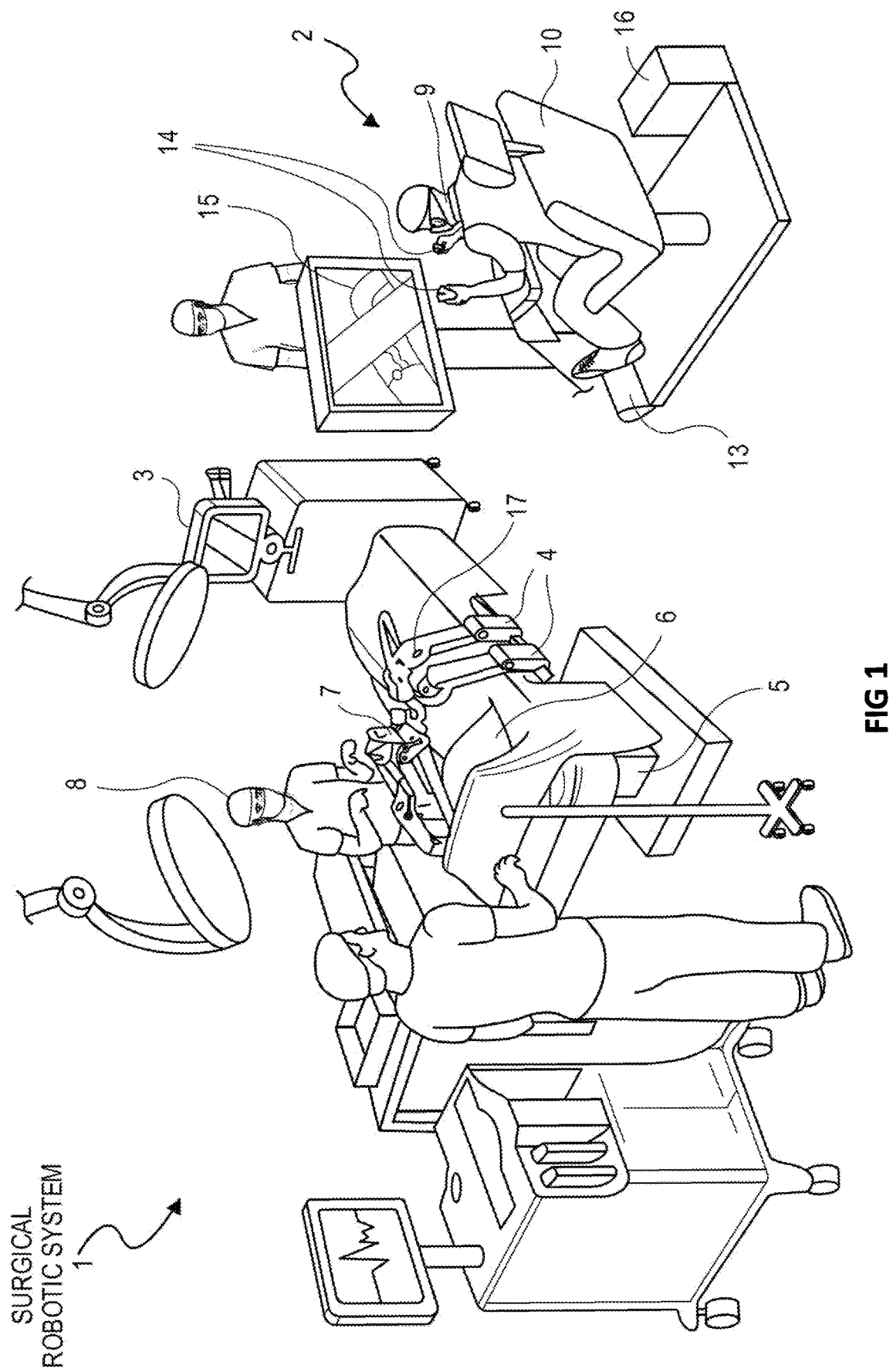
FIG. 1 shows an example of a surgical robotic system in an operating room, according to some embodiments.

Referring to FIG. 1, this is a pictorial view of an example surgical robotic system 1 in an operating arena. The system 1 includes a user console 2, a control tower 3, and one or more surgical robotic arms 4 at a surgical robotic platform 5, e.g., a table, a bed, etc. The arms 4 may be mounted to a table or bed on which the patient rests as shown in the example of FIG. 1, or they may be mounted to a cart separate from the table or bed. The system 1 can incorporate any number of devices, tools, or accessories used to perform surgery on a patient 6. For example, the system 1 may include one or more surgical tools 7 used to perform surgery. A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In one aspect, the surgical tool 7 is a grasper that can grasp tissue of the patient. The surgical tool 7 may be configured to be controlled manually by a bedside operator 8, robotically via actuated movement of the surgical robotic arm 4 to which it is attached, or both. The robotic arms 4 are shown as being table-mounted but in other configurations the arms 4 may be mounted to a cart, the ceiling or a sidewall, or to another suitable structural support.

A remote operator 9, such as a surgeon or other human operator, may use the user console 2 to remotely manipulate the arms 4 and their attached surgical tools 7, e.g., referred to here as teleoperation. The user console 2 may be located in the same operating room as the rest of the system 1 as shown in FIG. 1. In other environments however, the user console 2 may be located in an adjacent or nearby room, or it may be at a remote location, e.g., in a different building, city, or country. The user console 2 may comprise a seat 10, foot-operated controls 13, one or more handheld user input devices, UID 14, and at least one user display 15 that is configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the arms 4 and the surgical tools 7 that are mounted on the distal ends of the arms 4.

In some variations, the bedside operator 8 may operate the system 1 in an "over the bed" mode in which the beside operator 8 (user) is at a side of the patient 6 and is simultaneously manipulating a robotically-driven tool (an end effector that is attached to the arm 4) with a handheld UID 14 held in one hand, and a manual laparoscopic tool in another hand. For example, the bedside operator's left hand may be manipulating the handheld UID to control a robotically-driven tool, while the bedside operator's right hand may be manipulating a manual laparoscopic tool. In this particular variation of the system 1, the bedside operator 8 can perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the robotic system 1 are in a stowed configuration or withdrawn configuration (to facilitate access to the surgical site.) Once access is completed, initial positioning or preparation of the robotic system 1 including its arms 4 may be performed. Next, the surgery proceeds with the remote operator 9 at the user console 2 utilizing the foot-operated controls 13 and the UIDs 14 to manipulate the various end effectors and perhaps an imaging system, to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilization and healthcare record entry or printout via the user console 2.

In one embodiment, the remote operator 9 holds and moves the UID 14 to provide an input command to move a robot arm actuator 17 in the robotic system 1. The UID 14 may be communicatively coupled to the rest of the robotic system 1, e.g., via a console computer system 16. The UID 14 can generate spatial state signals corresponding to movement of the UID 14, e.g. position and orientation of the handheld housing of the UID, and the spatial state signals may be input signals to control a motion of the robot arm actuator 17. The robotic system 1 may use control signals derived from the spatial state signals, to control proportional motion of the actuator 17. In one embodiment, a console processor of the console computer system 16 receives the spatial state signals and generates the corresponding control signals. Based on these control signals, which control how the actuator 17 is energized to move a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn moves other linkages, gears, etc., of the robotic system 1. The robotic system 1 may include a right arm 4 that is secured to the bed or table to the right side of the patient, and a left arm 4 that is at the left side of the patient. An actuator 17 may include one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator, which opens or closes jaws of the grasper at a distal end of surgical tool 7 to grip tissue within patient 6.

In some aspects, the communication between the platform 5 and the user console 2 may be through a control tower 3, which may translate user commands that are received from the user console 2 (and more particularly from the console computer system 16) into robotic control commands that transmitted to the arms 4 on the robotic platform 5. The control tower 3 may also transmit status and feedback from the platform 5 back to the user console 2. The communication connections between the robotic platform 5, the user console 2, and the control tower 3 may be via wired and/or wireless links, using any suitable ones of a variety of data communication protocols. Any wired connections may be optionally built into the floor and/or walls or ceiling of the operating room. The robotic system 1 may provide video output to one or more displays, including displays within the operating room as well as remote displays that are accessible via the Internet or other networks. The video output (video feed) may also be encrypted to ensure privacy and all or portions of the video output may be saved to a server or electronic healthcare record system.

Figure 2:
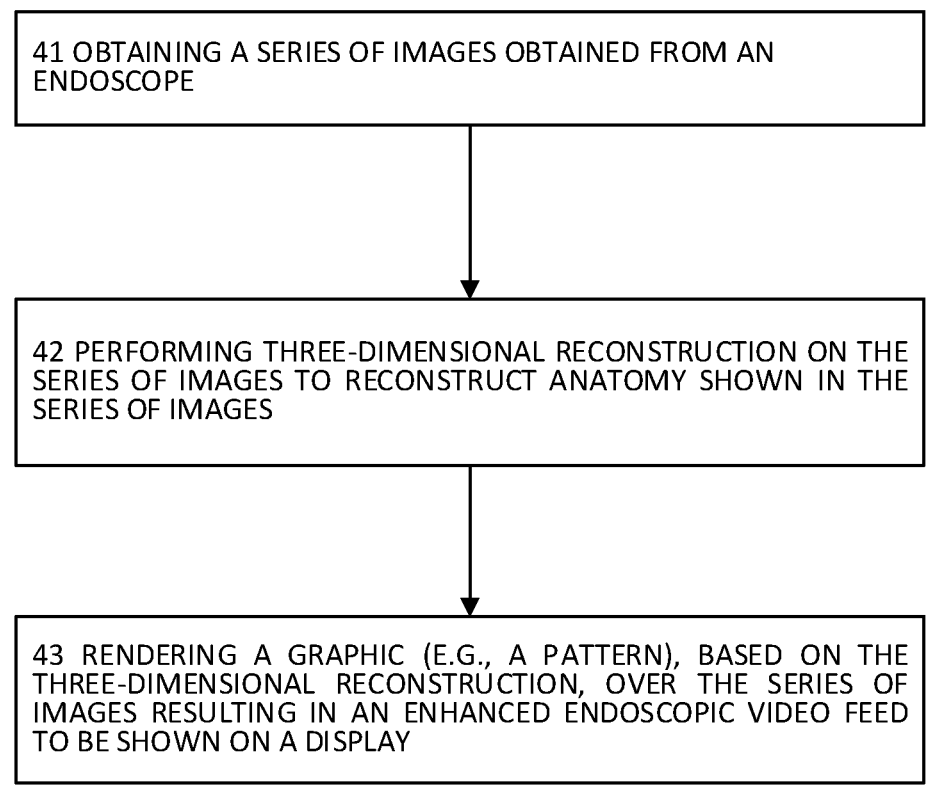
FIG. 2 shows a process for providing an enhanced endoscopic video feed, according to some embodiments.

In FIG. 2, a method or process 40 is shown that improves depth perception of an endoscopic feed. At operation 41, the process includes obtaining a series of images from an endoscope. The endoscope can have a single image sensor or a stereoscopic camera (having two or more lenses and associated image sensors). As described in other sections, if structured light is used for three-dimensional reconstruction, the endoscope can include a light source that emanates the structured light.

At operation 42, the process includes performing three-dimensional reconstruction on the series of images to reconstruct anatomy shown in the series of images. One or more techniques, such as structured lighting, machine learning, and/or stereoscopic reconstruction can be utilized to detect shape or surfaces of objects such as tools and anatomy captured in the series of images.

At operation 43, the process includes rendering a graphic, based on the three-dimensional reconstruction, over the series of images resulting in an enhanced endoscopic video feed to be shown on a display. For example, a pattern such as a grid can be projected onto one or more detected surfaces of the anatomy, determined based on the three-dimensional reconstruction.

The process can be performed repeatedly and in real-time (e.g., as the series of images are being captured by the endoscope) thereby providing improved depth perception and reducing risk of collisions during performance of a surgical procedure (or simulation thereof). In some embodiments, the process can be activated and deactivated through user input. In some embodiments, the process can be activated automatically based on sensed activity, such as changes in sensed light or movement, of the endoscope.

In some embodiments, the method can be performed with manual tools such as, for example, a manually controlled endoscope and other manually controlled surgical tools that enter a patient, for example, through a trocar. Additionally, or alternatively, the method can be performed with a surgical robotic system, such as the system described with reference to FIG. 1.

Figure 3:
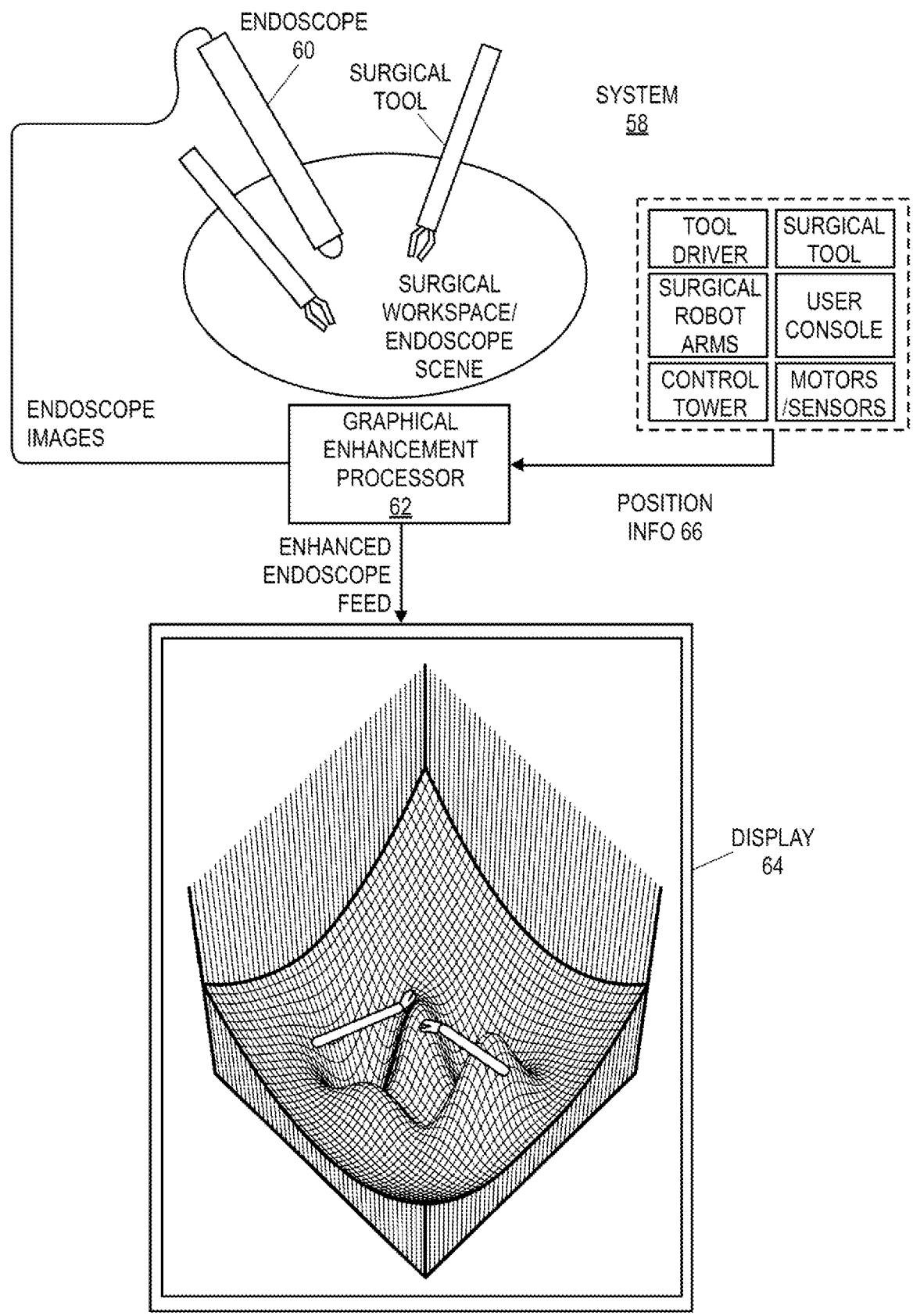
FIG. 3 illustrates a system for providing an enhanced endoscopic video feed, according to some embodiments.

In FIG. 3, a system 58 is shown for enhancing an endoscopic video feed. An endoscope 60 has one or more image sensors that generate a video feed (a sequence of images). When the endoscope is inserted in a patient, the internal anatomy of the patient is shown on the sequence of images. The internal anatomy can include tissue, organs, veins, capillaries, arteries, muscles, etc. The images can also include one or more surgical tools (e.g., endoscope, a scalpel, a grasper, or a needle).

A graphical enhancement processor 62 performs three-dimensional reconstruction on the endoscopic images to detect surfaces and shape of anatomy as well as objects such as the surgical tools. In some embodiments, such a processor can be integrated as part of the surgical robotic system shown in FIG. 1, for example, integrated with the user console 2, the control tower 3, or as a separate standalone computing device. Three-dimensional reconstruction can be performed using different techniques, such as, for example, those described below. It should be noted that other three-dimensional reconstruction approaches not discussed in the present disclosure can be implemented to reconstruct the endoscope scene without departing from the scope of the present disclosure.

In some embodiments, the three-dimensional reconstruction includes analyzing structured light that is captured in the series of images to reconstruct the anatomy. For example, a light projector can illuminate the scene captured by the endoscope with a 2D pattern that can have a spatially varying intensity pattern. The light projector can be integrated with the endoscope or a separate tool that is inserted in the patient. Surface that the light pattern falls upon will alter the shape of the light pattern as detected by the endoscope camera. This structured light that falls upon the surface can be analyzed to detect the shape of the surface in the scene, thereby reconstructing the three-dimensional surface shape of the internal anatomy of the patient, as well as objects such as tools that are present in the scene.

In some embodiments, the endoscope can include a stereo camera having at least two lenses and corresponding image sensors at different vantage points. The three-dimensional reconstruction can be performed by establishing stereo correspondence between images captured by each image sensor of the stereo camera to three-dimensionally reconstruct the surface shapes of the internal anatomy of the patient. Similarly, as objects such as tools that are present in the scene can be reconstructed in the same manner.

For example, known computer vision algorithms can be applied to the image streams of the endoscope's stereo camera. The binocular stereo vision of the endoscopic images can be leveraged as the two or more cameras of the endoscope acquire images from different vantage points. From the two image streams, the corresponding feature points (e.g., a common mark or 'feature' captured in both image streams) can be extracted for reconstruction. The 3D positions of these feature points can be calculated based on the disparity of the images and the geometric relationship between the two viewpoints, thus establishing and using stereo correspondence between the image streams to reconstruct the anatomy and objects captured in the images.

In some embodiments, the surgical robotic system of FIG. 1 can include such an endoscope with a stereo camera. This endoscope can be manually operated or attached as a tool 7 to one or more of the surgical robot arms 4.

In some embodiments, the relative positions and orientations of the tools with respect to the endoscopic view may be obtained from geometry computation from the surgical robot arms and tool drivers that effects movement in one or more surgical tools that are shown in the series of images. For example, referring to FIG. 3, position information 66 of the tools shown in the endoscopic feed can be obtained from motor positions and sensors that effect, encode, and/or sense position of the surgical robotic arms and the tools attached to the distal ends of those arms. Telemetry can be obtained describing the position (e.g., joint values) of the surgical robotic arms and attached tools, which can be transformed, using kinematic data of the surgical robotic arms, to determine three dimensional orientation and position data of the surgical robotic arms and tools. In some embodiments, the position information can be obtained from the user console, control tower, or other components described with respect to FIG. 1.

The position information 66 obtained from the surgical robotic system can be mapped to the endoscopic view to improve accuracy of the three dimensional reconstruction of the endoscopic scene. The system can compare derived positions of the tools and anatomy to assess, and improve the three-dimensional reconstruction, by providing corroborating or contradicting data points. Additionally, or alternatively, the tool positions can be determined through processing the endoscope feed with computer vision algorithms, by recognizing the tools in the endoscopic feed and/or through other three-dimensional reconstruction approaches known or described in the present disclosure.

Referring to FIG. 3, in some embodiments, the three-dimensional reconstruction performed at graphical enhancement processor 62 includes applying a machine learning model to the series of images to reconstruct the anatomy. The machine learning model can include an artificial neural network such as a convolutional neural network, a feed-forward neural network, or recurrent neural network. The model can be trained with training data to detect and reconstruct 3D surfaces present in the endoscopic scene. The trained neural network can map the information in the endoscopic images to underlying 3D shapes.

In some embodiments, the three-dimensional reconstruction includes estimating geometry of the environment based on 3D registration (e.g., point set registration) and reconstruction using the endoscope images. Additional geometry information from other sensor scans (e.g., MRI or CT scans) can also be utilized to improve the accuracy of the 3D reconstruction.

The graphical enhancement processor 62 renders a graphic, based on the three-dimensional reconstruction, over the series of images resulting in an enhanced endoscopic video feed to be shown on the display 64. For example, the graphic can include a pattern, such as a grid (also describable as a mesh), lines, dots, or polygons, projected onto one or more detected surfaces of the anatomy. Further, although shown in the figures as rectangular, the grid can include other shapes such as triangles, and other polygons. The display can include a stereoscopic display, a 2D display, and/or a head worn display, such as, for example, virtual reality or augmented reality head worn device.

In some embodiments, the display is integrated with the surgical robotic system shown in FIG. 1, such as display 15 of the user console. In some embodiments, this display is a stereoscopic display. In some embodiments, the stereoscopic display is head worn. The display can facilitate performance of remote surgery. Additionally, or alternatively, a display can be present at the table-side, as a standalone 2D display, or as a head worn device, to help guide manually controlled tools by a bedside operator 8.

Figure 4:
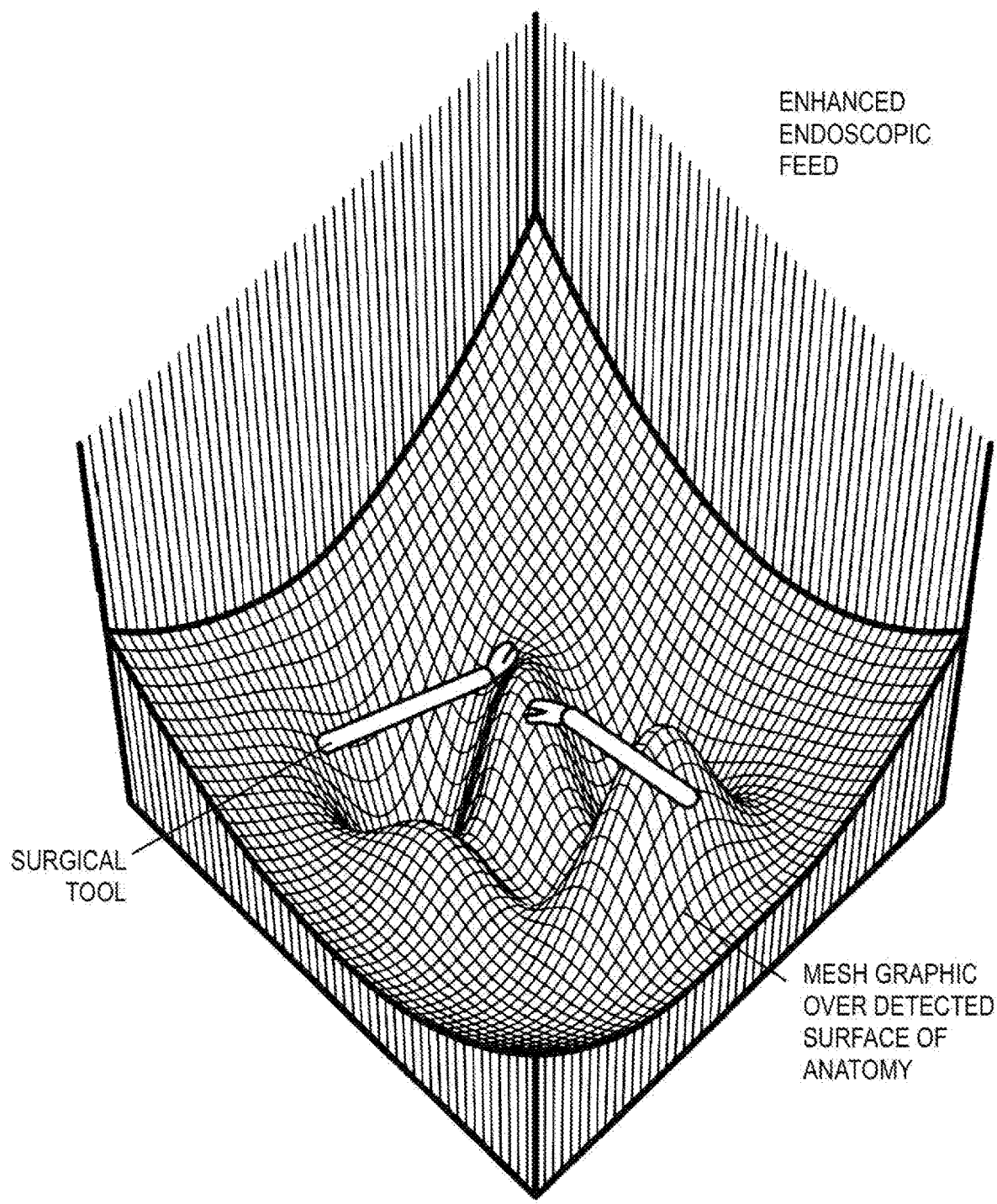
FIG. 4 illustrates an enhanced endoscopic feed, according to some embodiments.

An example of an enhanced endoscopic feed is shown in FIG. 4. A mesh or grid is rendered over a detected surface (e.g., objects or anatomy) in the endoscopic scene. In this manner, the visibility of shape and location of surfaces of the anatomy is improved.

Figure 5:
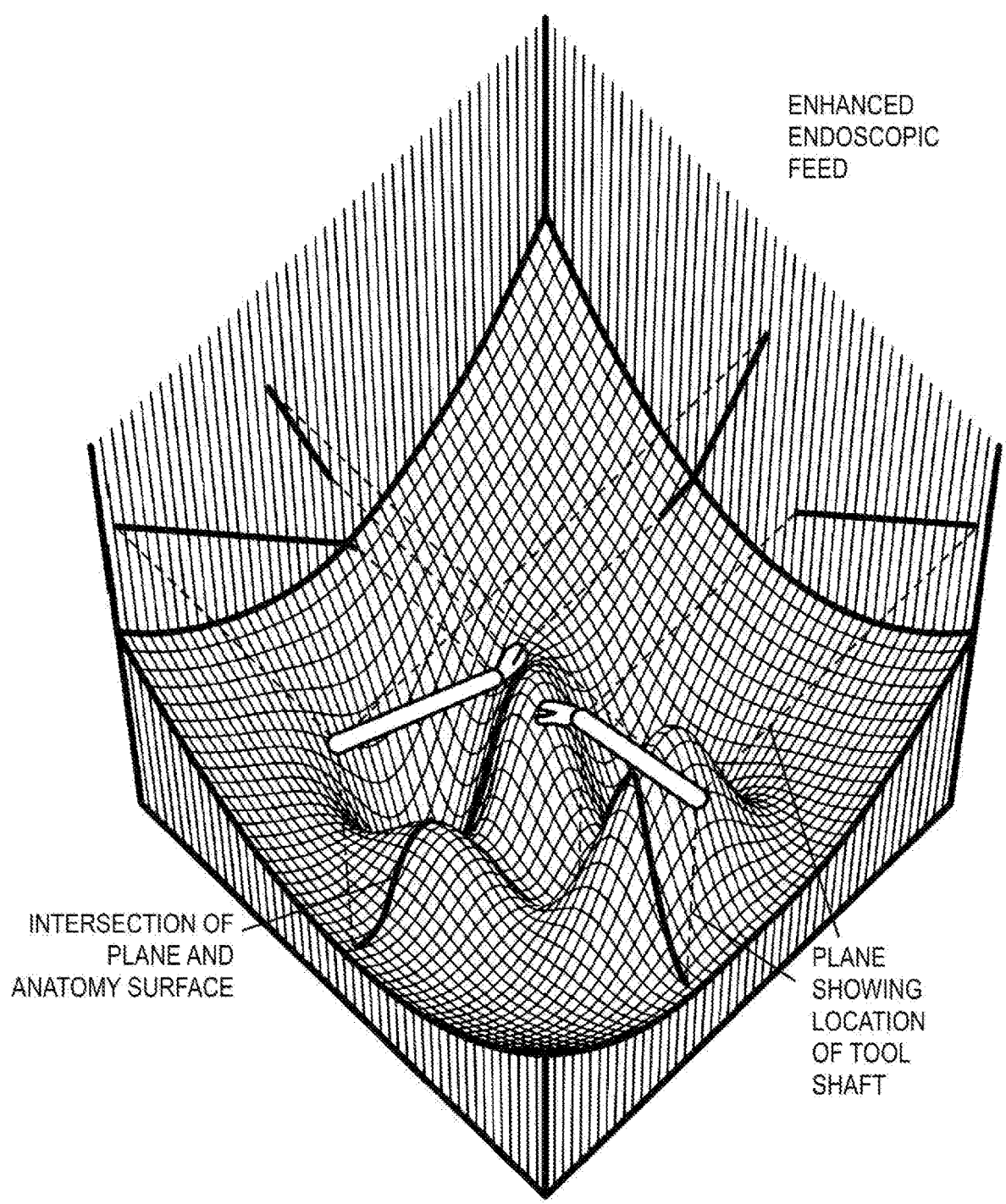
FIG. 5 illustrates an enhanced endoscopic feed, with graphics indicating position of one or more tools, according to some embodiments.

Another example of an enhanced endoscopic feed is shown in FIG. 5. In this enhanced endoscopic feed, the graphic includes one or more lines that show a position of a surgical tool that is captured in the series of images. For example, lines (e.g., the dashed lines) can show one or more planes originating from the axis of the tool shaft. Other lines (e.g., the thick solid line) show intersection of these planes with the surface of anatomy. These graphics serve as a geometric reference showing distance between the tool and the anatomy along the plane. The pattern projected onto the surface of the user's anatomy further helps a user discern distances between the tool and the anatomy relative to the intersection line. Thus, depth perception can be improved, and risk of collision can be reduced.

Figure 6:
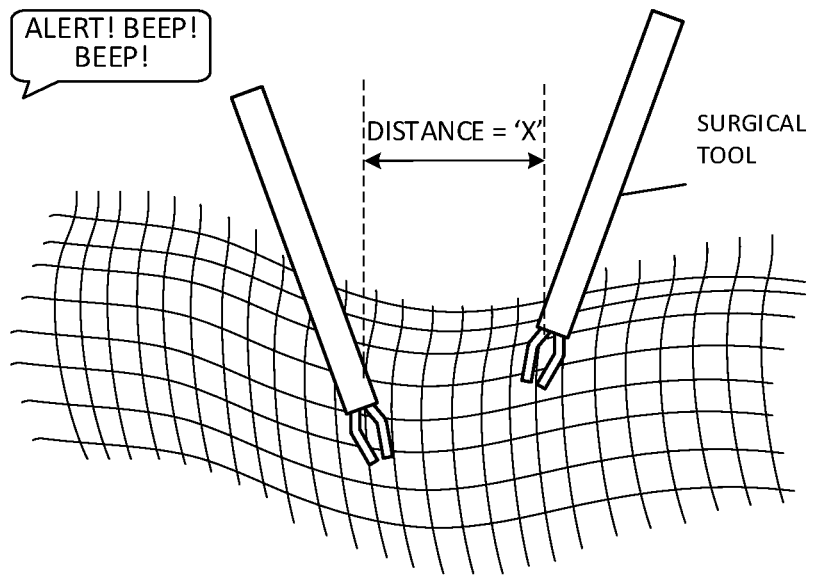
FIG. 6 and FIG. 7 show an enhanced endoscopic feed with warning system, according to some embodiments.

In some embodiments, a user can enable positional references such as quantitative position, orientation, or distance measurement of any element of the endoscopic scene, the anatomy of the patient, and tools. Numerical texts can be displayed next to the feature. For example, text or a graphic can be rendered in the enhanced endoscopic feed showing distance between two tools (e.g., between the end effectors, the tool shaft, and/or the overall shortest distance between the tools) as shown in FIG. 6. Similarly, the relative position of an object in the scene can be rendered as text in the enhanced endoscopic feed.

In some embodiments, as shown in FIG. 6, visual or audio warning could be implemented for potential risks of collision of various elements in the scene. For example, a visual or audio warning is given if a tool is determined to be within a threshold proximity to another tool.

Figure 7:
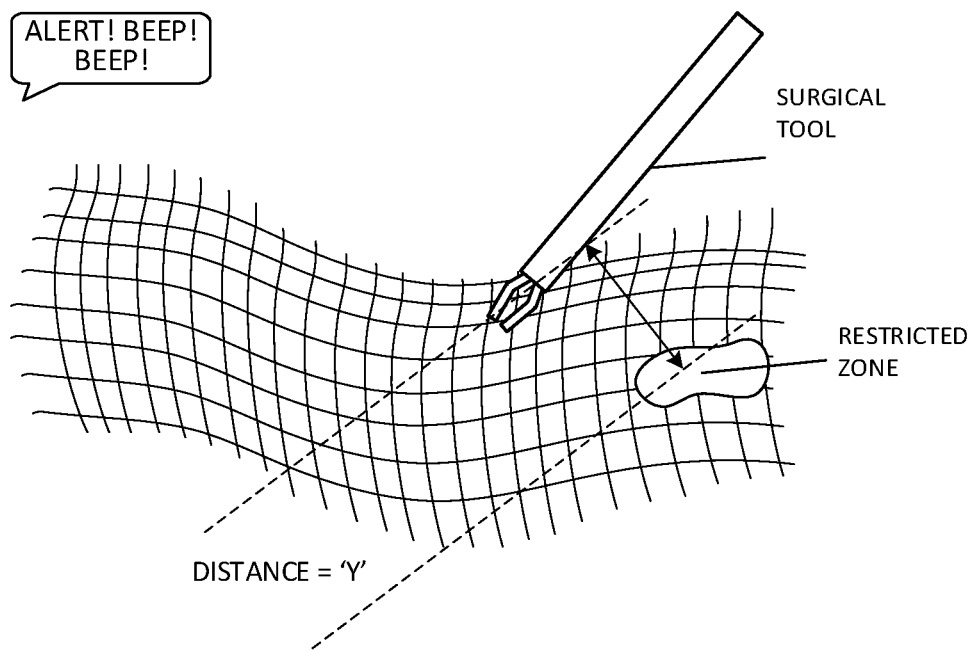

Similarly, as shown in FIG. 7, text or graphics can show a distance between a tool and the anatomy that is captured in the series of images. Organs or zones of the anatomy can be identified (e.g., by a user input, or a configurable setting) as 'restricted' or 'of interest' such that the distance will be shown between the tool and the area of interest. The system can provide a visual or audio warning if the tool is determined to be within a threshold proximity to the restricted or 'of interest' zone. In some aspects, if a tool is inactive and is determined to be within a threshold proximity to an organ or a specified zone, then a warning can be made. The thresholds described above can be specified through different means, for example, they can be configurable as a setting, specified through user input, and/or hard coded in programmable memory.

In some embodiments, based on the 3D reconstruction, computer vision algorithms, and/or position information of surgical tools received from a surgical robotic system, the system can determine that one of the thresholds described above has been satisfied. In this case, a text warning can be flashed to the display and/or an audible warning can be provided with a speaker, stating the warning, for example, that the tools are within 'x' distance of each other. In some cases, a line or other graphic can be rendered showing the shortest path between the tools (or between the tool and the anatomy). This can inform the user as to how to move the tool to increase separation.

Various embodiments and components described herein may be embodied, at least in part, in software. That is, the processes may be carried out by a processor executing a sequence of instructions contained in a storage medium, such as a non-transitory machine-readable storage medium (e.g. DRAM or flash memory). In various embodiments, hardwired circuitry may be used in combination with software instructions to implement the techniques described herein. Thus the techniques are not limited to any specific combination of hardware circuitry and software, or to any particular source for the instructions executed by the audio processing system.

In the description, certain terminology is used to describe features of various embodiments. For example, in certain situations, the terms "module", "processor", "unit", "model", "system", "device", and "component," are representative of hardware and/or software configured to perform one or more processes or functions. For instance, examples of "hardware" include, but are not limited or restricted to an integrated circuit such as a processor (e.g., a digital signal processor, microprocessor, application specific integrated circuit, a micro-controller, etc.). Thus, different combinations of hardware and/or software can be implemented to perform the processes or functions described by the above terms, as understood by one skilled in the art. Of course, the hardware may be alternatively implemented as a finite state machine or even combinatorial logic. An example of "software" includes executable code in the form of an application, an applet, a routine or even a series of instructions. As mentioned above, the software may be stored in any type of machine-readable medium.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, and they thereby enable others skilled in the art to best utilize the invention and various embodiments with various modifications as are suited to the particular use contemplated.

What is claimed is:

1. A method, including:
   obtaining a series of images of an internal anatomy obtained from an endoscope;
   performing three-dimensional reconstruction on the series of images to reconstruct surface shapes of a portion of the internal anatomy shown in the series of images;
   rendering a graphic, based on the three-dimensional reconstruction, that includes a pattern projected over the surface shapes of the portion of the internal anatomy shown in the series of images resulting in an enhanced endoscopic video feed; and
   displaying the enhanced endoscopic video feed on a display.

2. The method of claim 1, wherein the pattern includes at least one: of a grid, lines, and dots.

3. The method of claim 1, wherein the graphic includes one or more lines that show a position of a surgical tool that is captured in the series of images.

4. The method of claim 1, wherein the series of images comprise at least one surgical tool, wherein the graphic indicates at least one of: a distance between two or more surgical tools in the series of images, or a distance between the at least one surgical tool and the internal anatomy in the series of images.

5. The method of claim 1, further comprising, providing a visual warning on the display or an audio warning on a speaker if a tool captured in the series of images is determined to be within a threshold proximity to a) another tool captured in the series of images, or b) a specified zone of the anatomy.

6. The method of claim 1, wherein the endoscope includes a stereo camera having at least two lenses and corresponding image sensors at different vantage points, and the three-dimensional reconstruction includes establishing stereo correspondence between images of the stereo camera to reconstruct the surface shapes of the portion of the internal anatomy.

7. The method of claim 1, wherein performing three-dimensional reconstruction includes obtaining position information from a surgical robotic arm or a tool driver that effects movement in one or more surgical tools that are shown in the series of images, to determine position the one or more surgical tools.

8. The method of claim 1, wherein the three-dimensional reconstruction includes analyzing structured light that is captured in the series of images to reconstruct the surface shapes of the portion of the internal anatomy.

9. The method of claim 1, wherein the three-dimensional reconstruction includes applying a machine learning model to the series of images to reconstruct the surface shapes of the portion of the internal anatomy.

10. The method of claim 1, wherein the series of images includes one or more manually operated surgical tools.

11. The method of claim 1, wherein the display is a stereoscopic display.

12. A system, comprising:
    one or more surgical robotic arms;
    an endoscope;
    a display; and
    a processor, configured to perform the following:
       performing three-dimensional reconstruction on a series of images that includes an internal anatomy of a patient obtained from the endoscope to reconstruct surface shapes of a portion of the internal anatomy shown in the series of images;
       rendering a graphic, including a pattern projected onto one or more detected surfaces of the portion of the internal anatomy determined based on the three-dimensional reconstruction, over the series of images resulting in an enhanced endoscopic video; and
       displaying the enhanced endoscopic video on the display.

13. The system of claim 12, wherein performing three-dimensional reconstruction includes obtaining position information from the one or more surgical robotic arms or a tool driver that effects movement in one or more surgical tools that are attached to the one or more surgical robotic arms and shown in the series of images, to determine position of the one or more surgical tools.

14. The system of claim 12, wherein the pattern includes at least one: of a grid, lines, and dots.

15. The system of claim 12, wherein the graphic includes one or more lines that show a position of a surgical tool, coupled to the one or more surgical robotic arms, that is captured in the series of images.

16. The system of claim 12, wherein the series of images comprise at least one surgical tool, wherein the graphic indicates at least one of: a distance between two or more surgical tools in the series of images, or a distance between the at least one surgical tool and the internal anatomy in the series of images.

17. The system of claim 12, further comprising, providing a visual or audio warning if a surgical tool is determined to be within a threshold proximity to a) another surgical tool, or b) a specified zone of the internal anatomy.

18. The system of claim 12, wherein the endoscope includes a stereo camera having least two lenses and corresponding image sensors at different vantage points, and the three-dimensional reconstruction includes establishing stereo correspondence between images of the stereo camera to reconstruct the surface shapes of a portion of the internal anatomy.

19. The system of claim 12, wherein the display includes at least one of: a stereoscopic display, a 2D display, and a head worn display.

* * * * *